United States Patent
Kim et al.

(10) Patent No.: US 11,583,559 B2
(45) Date of Patent: Feb. 21, 2023

(54) **COMPOSITION FOR PREVENTING OR TREATING MENTAL DISORDER, CONTAINING *LACTOBACILLUS* SP. BACTERIA-DERIVED VESICLE**

(71) Applicant: MD HEALTHCARE INC., Seoul (KR)

(72) Inventors: Yoon-Keun Kim, Gyeonggi-do (KR); Pyung lim Han, Seoul (KR); Ju-Li Choi, Seoul (KR)

(73) Assignee: MD HEALTHCARE INC., Seoul (KR)

( * ) Notice: Subject to any disclaimer, the term of this patent is extended or adjusted under 35 U.S.C. 154(b) by 142 days.

(21) Appl. No.: 16/325,884

(22) PCT Filed: Aug. 9, 2017

(86) PCT No.: PCT/KR2017/008652
§ 371 (c)(1),
(2) Date: Feb. 15, 2019

(87) PCT Pub. No.: WO2018/034457
PCT Pub. Date: Feb. 22, 2018

(65) Prior Publication Data
US 2019/0209628 A1    Jul. 11, 2019

(30) Foreign Application Priority Data

Aug. 16, 2016  (KR) .................. 10-2016-0103680
Jul. 4, 2017   (KR) .................. 10-2017-0085020
Aug. 8, 2017   (KR) .................. 10-2017-0100459

(51) Int. Cl.
| | | |
|---|---|---|
| A61K 35/747 | (2015.01) | |
| A61K 9/127 | (2006.01) | |
| A61P 25/24 | (2006.01) | |
| A61P 25/22 | (2006.01) | |
| A61P 25/18 | (2006.01) | |
| A61K 9/00 | (2006.01) | |
| A23L 33/135 | (2016.01) | |

(52) U.S. Cl.
CPC .......... *A61K 35/747* (2013.01); *A23L 33/135* (2016.08); *A61K 9/0073* (2013.01); *A61K 9/127* (2013.01); *A61P 25/18* (2018.01); *A61P 25/22* (2018.01); *A61P 25/24* (2018.01)

(58) Field of Classification Search
None
See application file for complete search history.

(56) References Cited

U.S. PATENT DOCUMENTS

| | | | | |
|---|---|---|---|---|
| 10,406,184 B2 * | 9/2019 | Kim | ............. | A61K 35/747 |
| 2004/0247581 A1 * | 12/2004 | Bronstad | .......... | A61P 25/00 |
| | | | | 435/7.32 |
| 2007/0104738 A1 | 5/2007 | Tatischeff et al. | | |
| 2015/0056246 A1 * | 2/2015 | Putnam | ............. | A61K 39/39 |
| | | | | 424/200.1 |

FOREIGN PATENT DOCUMENTS

| | | | |
|---|---|---|---|
| CN | 103550778 | 2/2014 | |
| EP | 0966969 A1 | 12/1999 | |
| EP | 2332539 A1 | 6/2011 | |
| EP | 2937424 A1 | 10/2015 | |
| EP | 2484752 B1 * | 9/2016 | ............... A61P 9/10 |
| JP | 2002544146 A | 12/2002 | |
| JP | 2006525313 A | 11/2006 | |
| JP | 2008081434 A | 4/2008 | |
| JP | 2011116666 A | 6/2011 | |
| KR | 20090041889 A | 4/2009 | |
| KR | 10-2011-0025603 A | 3/2011 | |
| KR | 20110025603 A * | 3/2011 | .............. A61P 31/04 |
| KR | 20110025603 A | 3/2011 | |
| KR | 10-2011-0082481 A | 7/2011 | |
| KR | 20110082481 A | 7/2011 | |
| KR | 20110082481 A * | 7/2011 | ............. A61K 35/37 |
| WO | 2004098622 A2 | 11/2004 | |
| WO | 2005077391 A1 | 8/2005 | |

(Continued)

OTHER PUBLICATIONS

Stephanie A. Flowers et al., "The Microbiome in Mental Health: Potential Contribution of Gut Microbiota in Disease and Pharmacotherapy Management", Pharmacotherapy, Oct. 2015; vol. 35(10) pp. 910-916.

Schertzer, J. W. et al, 'Bacterial outer membrane vesicles in trafficking, communication and the host-pathogen interaction', Journal of Molecular Microbiology and Biotechnology, 2013, vol. 23, pp. 118-130.

Brown, L. et al., 'Extracellular vesicles produced by the Gram-positive bacterium Bacillus subtilis are disrupted by the lipopeptide surfactin', Molecular Microbiology, 2014, vol. 93(1), pp. 183-198.

Zaborowski, M. P. et al., 'Extracellular vesicles: composition, biological relevance, and methods of study', BioScience, 2015, vol. 65(8), pp. 783-797.

(Continued)

*Primary Examiner* — Nghi V Nguyen
(74) *Attorney, Agent, or Firm* — Riverside Law LLP

(57) ABSTRACT

The present invention relates to a composition for preventing, improving or treating a mental disorder, the composition containing a *Lactobacillus* sp. bacteria-derived vesicle as an active ingredient. The present inventors have confirmed that, when a *Lactobacillus* sp. bacteria-derived vesicle is administered to a stress and depression animal model, resistance to stress efficiently increases, and an effect of treating chronically persisting long-term depression behavior is exhibited, and thus the *Lactobacillus* sp. bacteria-derived vesicle, according to the present invention, is expected to be capable of being usefully employed in developing a medicine or a functional health food, etc., for preventing, reducing the symptoms of or treating a mental disorder such as stress, anxiety disorder, post-traumatic stress disorder, panic disorder, depression, autism spectrum disorder, attention deficit hyperactivity disorder and schizophrenia.

6 Claims, 21 Drawing Sheets

(56) References Cited

FOREIGN PATENT DOCUMENTS

| WO | 2008155998 A1 | 12/2008 | | |
|---|---|---|---|---|
| WO | 2010021247 A1 | 2/2010 | | |
| WO | 2010060722 A1 | 6/2010 | | |
| WO | 2012089784 A1 | 7/2012 | | |
| WO | 2014132982 A1 | 9/2014 | | |
| WO | 2016065419 | 5/2016 | | |
| WO | 2016065419 A1 | 5/2016 | | |
| WO | WO-2016065419 A1 * | 5/2016 | ............... | A23L 2/52 |
| WO | 2016124642 A1 | 8/2016 | | |

OTHER PUBLICATIONS

Liu Yen-Wenn et al., "Psychotropic effects of Lactobacillus plantarum PS128 in early life-stressed and naïve adult mice", Brain Research, 2016, 1631:1-12.

Eutamene H et al., "Synergy between Lactobacillus paracasei and its bacterial products to counteract stress-induced gut permeability and sensitivity increase in rats", The Journal of Nutrition, 2007, 137(8):1901-1907.

Lutgendorff Femke et al., "The role of microbiota and probiotics in stress-induced gastro-intestinal damage", Current Morecular Medicine, 2008, 8(4):282-298.

* cited by examiner

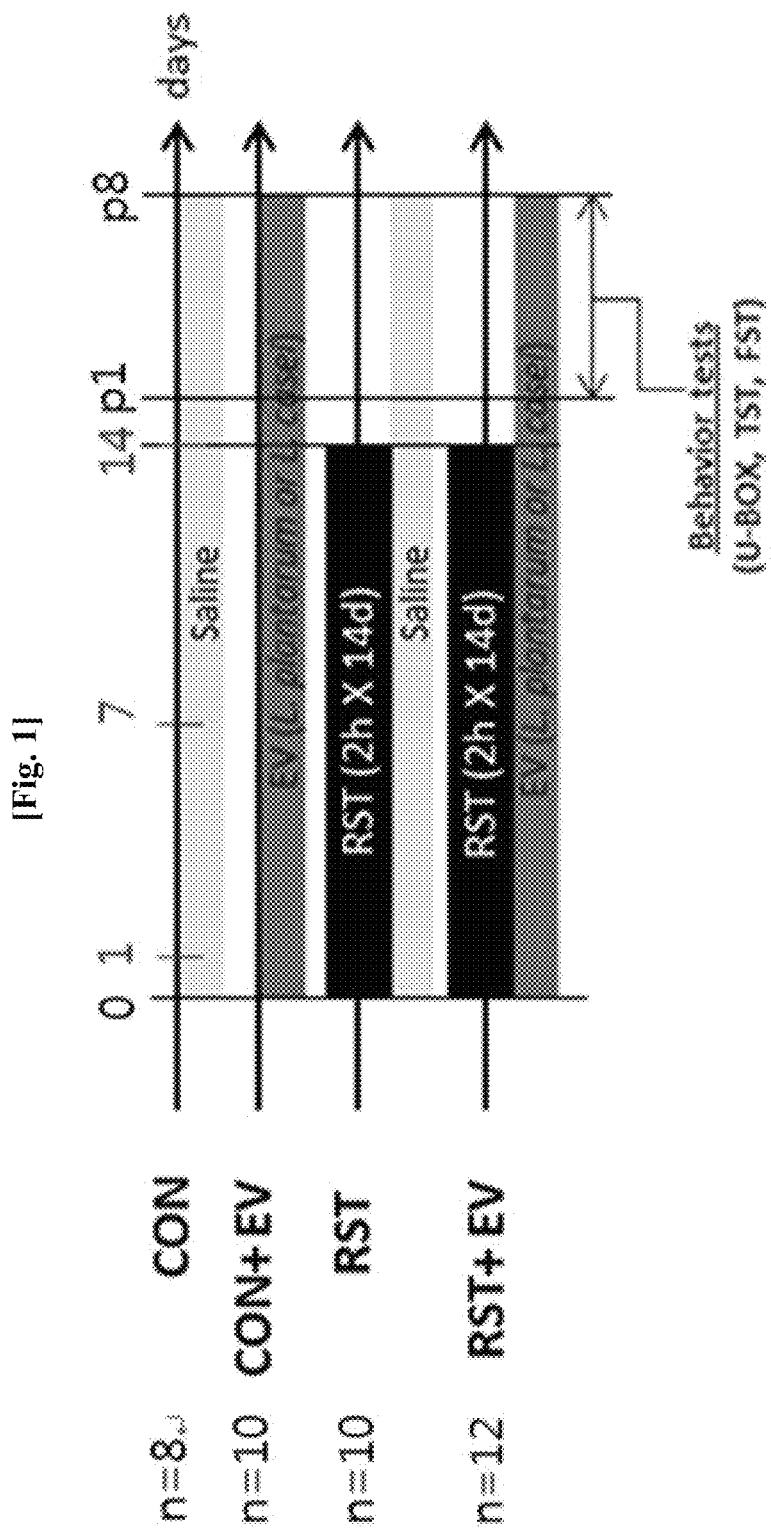

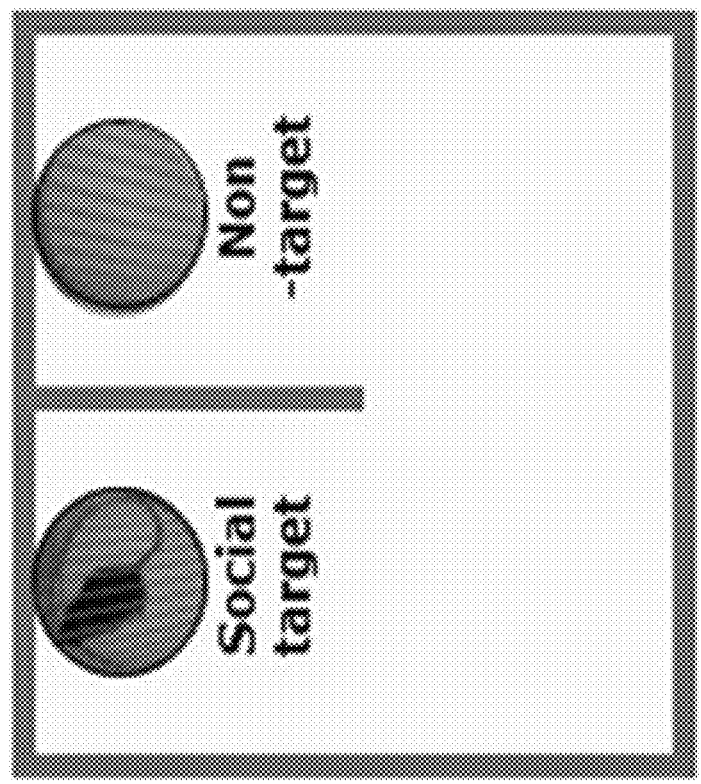
[Fig. 2A]

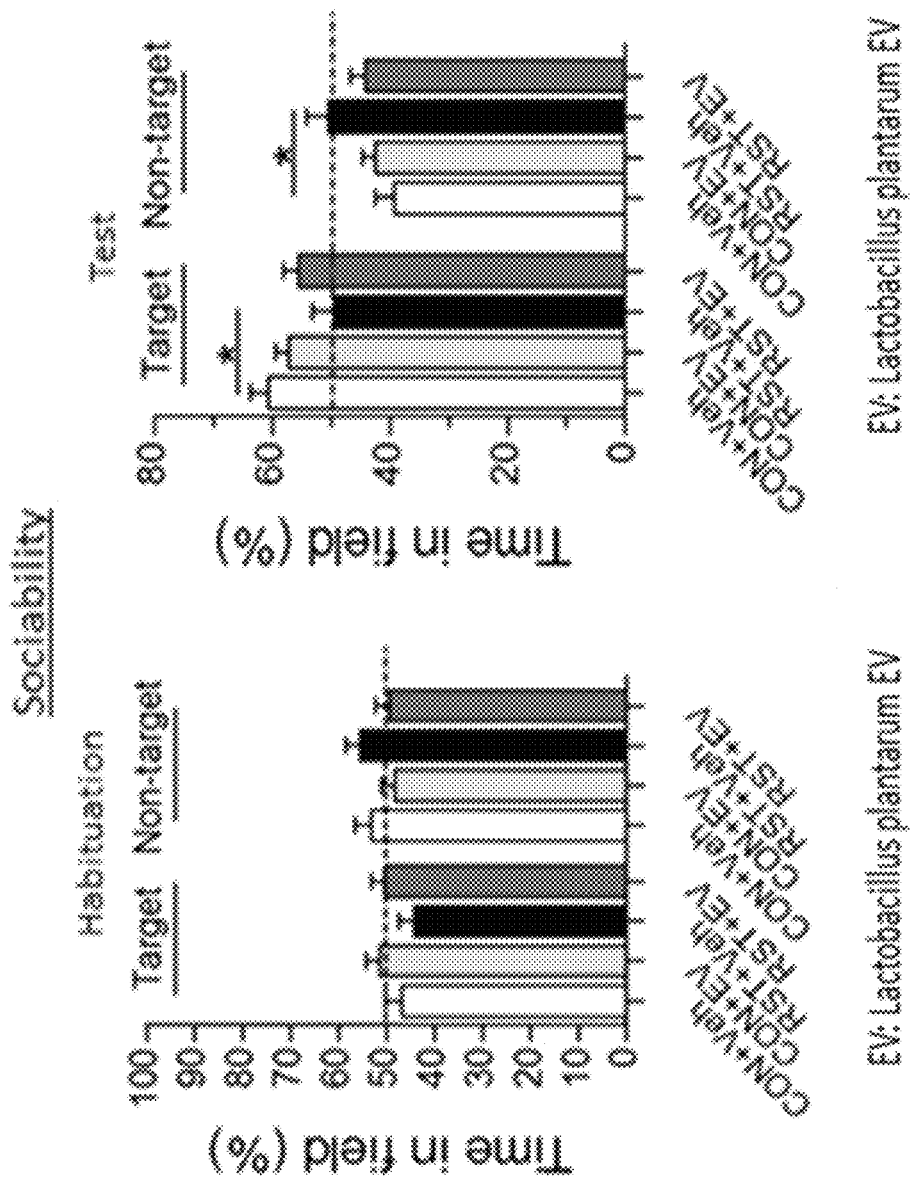

[Fig. 3A]
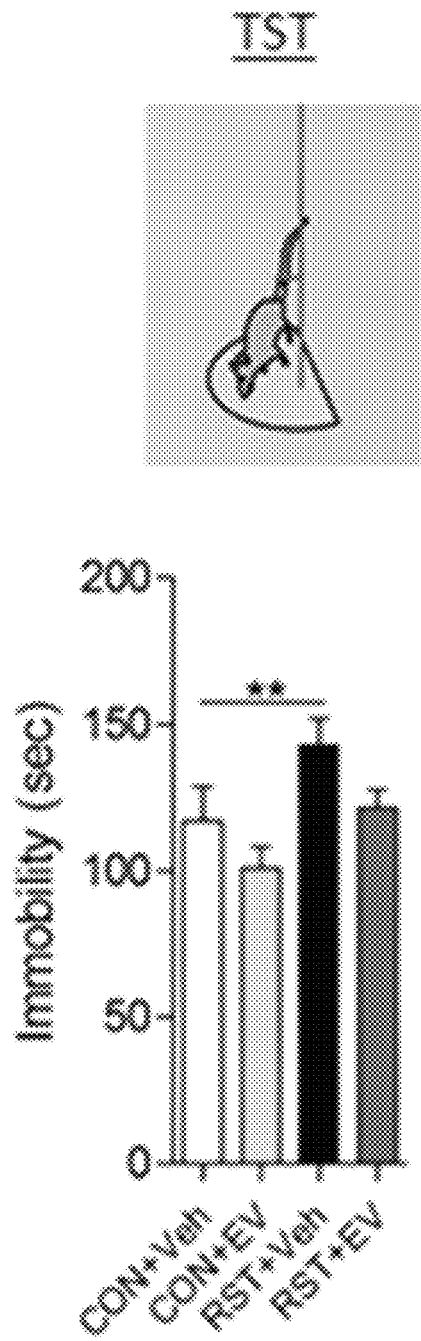
EV: Lactobacillus plantarum EV

[Fig. 3B]
FST
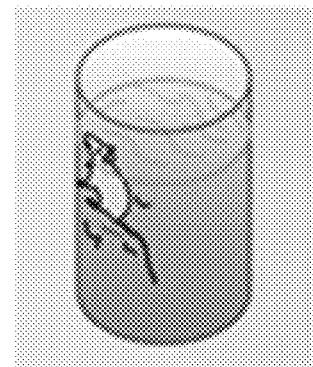
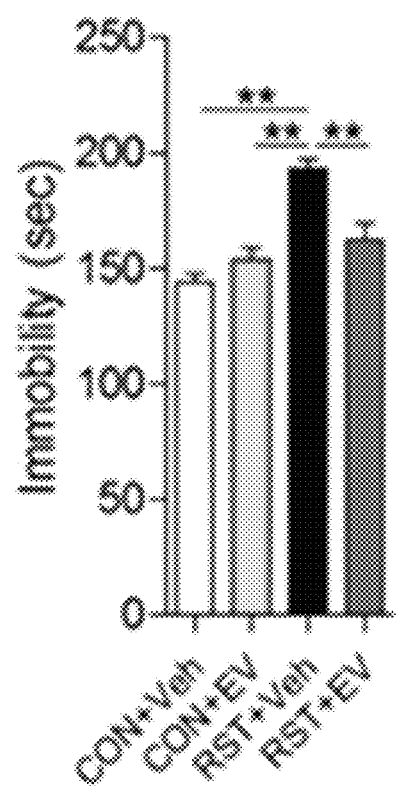
EV: Lactobacillus plantarum EV

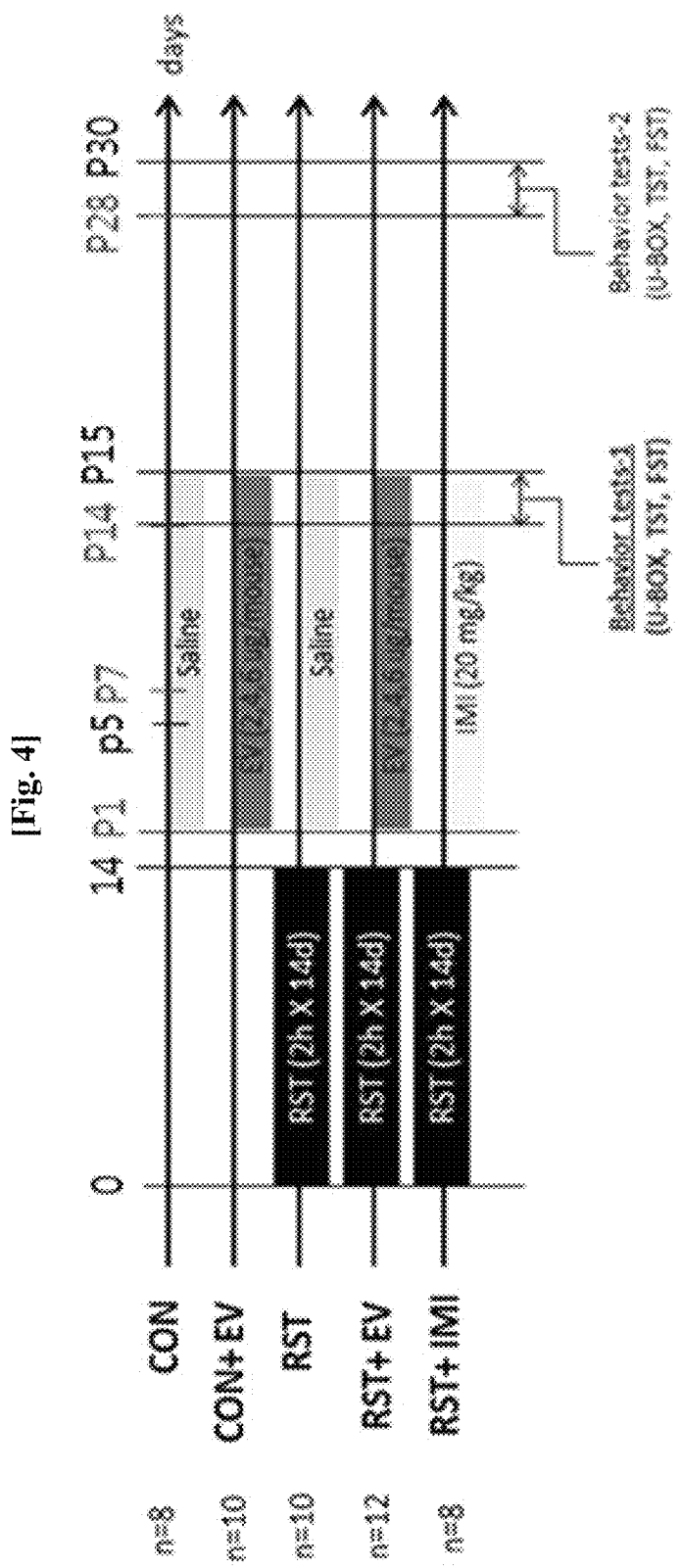

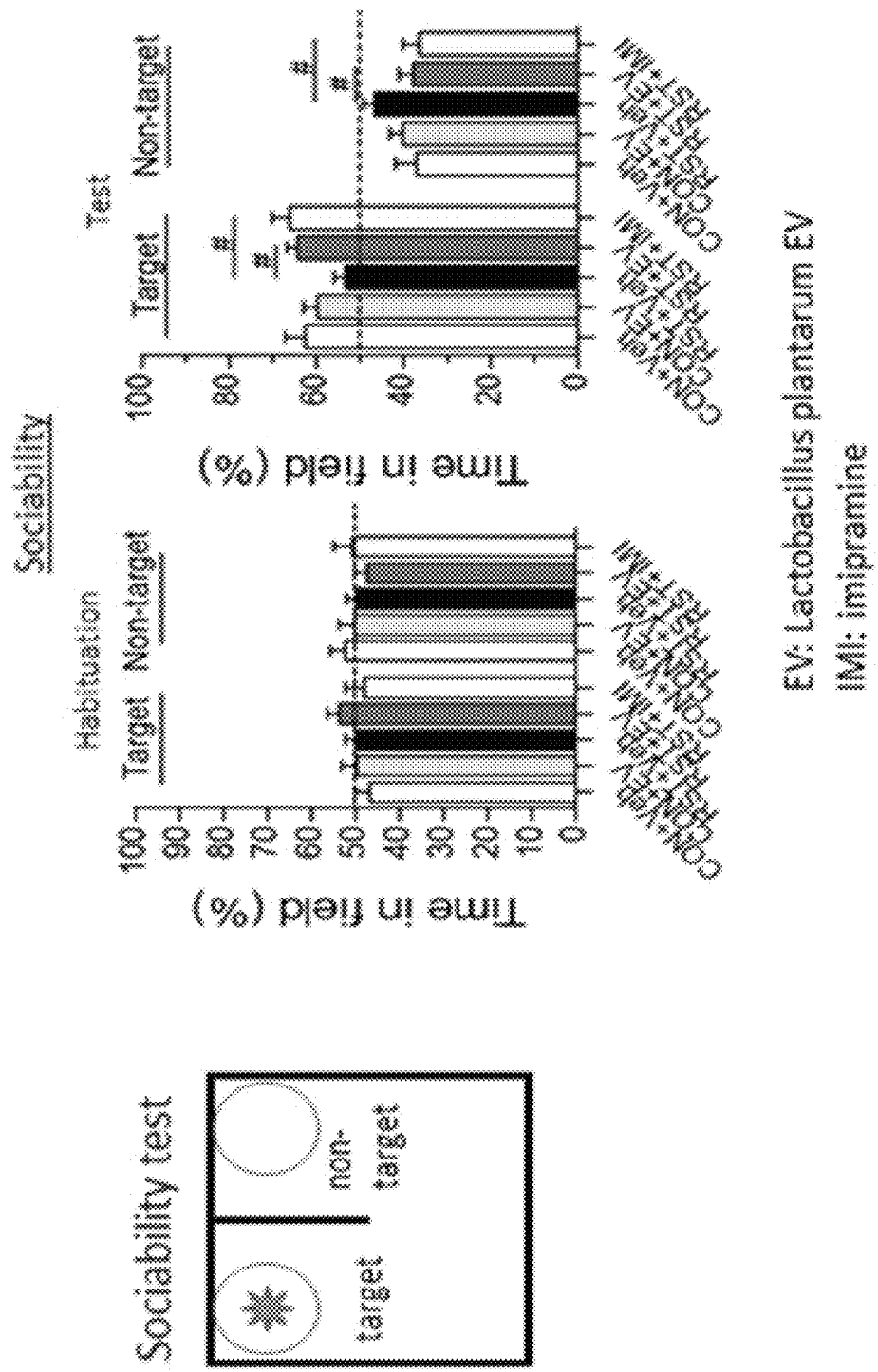
[Fig. 5]

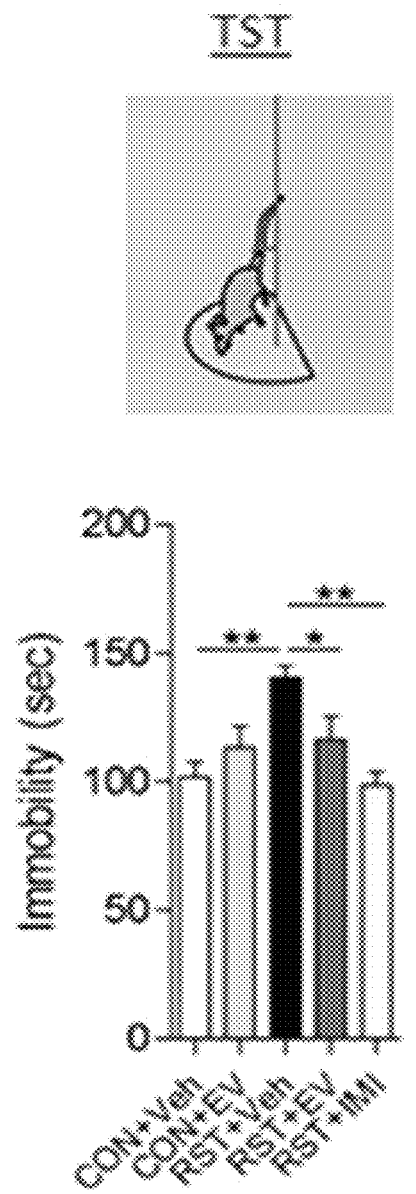
[Fig. 6A]
EV: Lactobacillus plantarum EV
IMI: imipramine

[Fig. 6B]
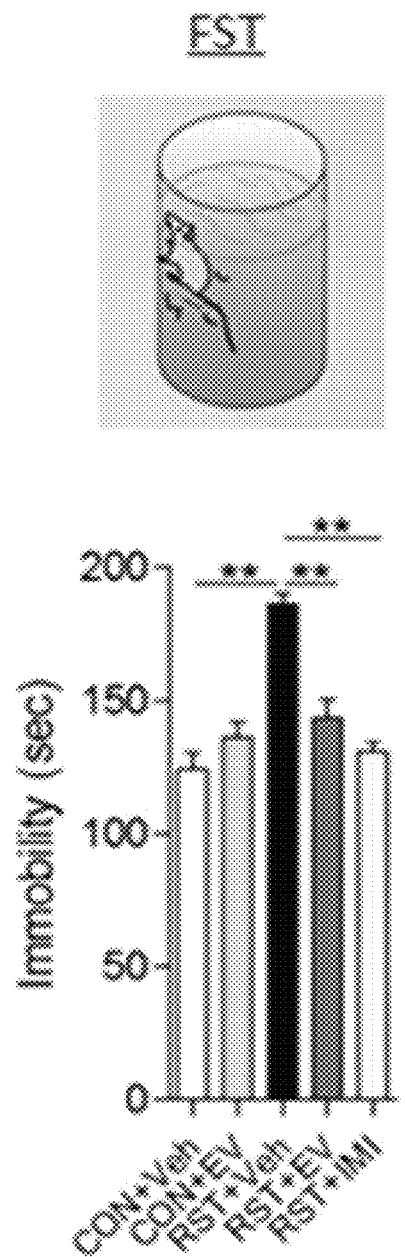
EV: Lactobacillus plantarum EV
IMI: imipramine

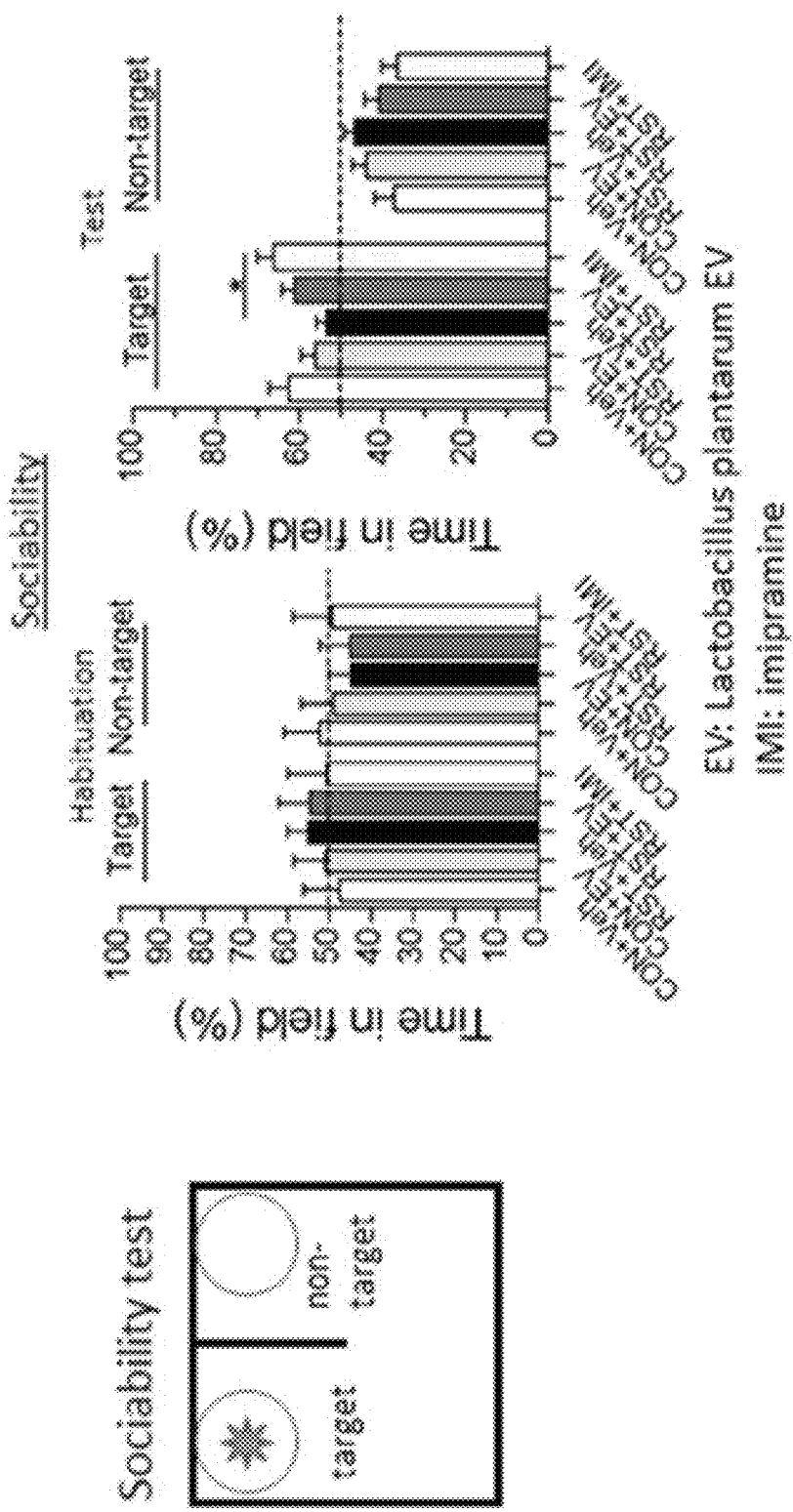
[Fig. 7]

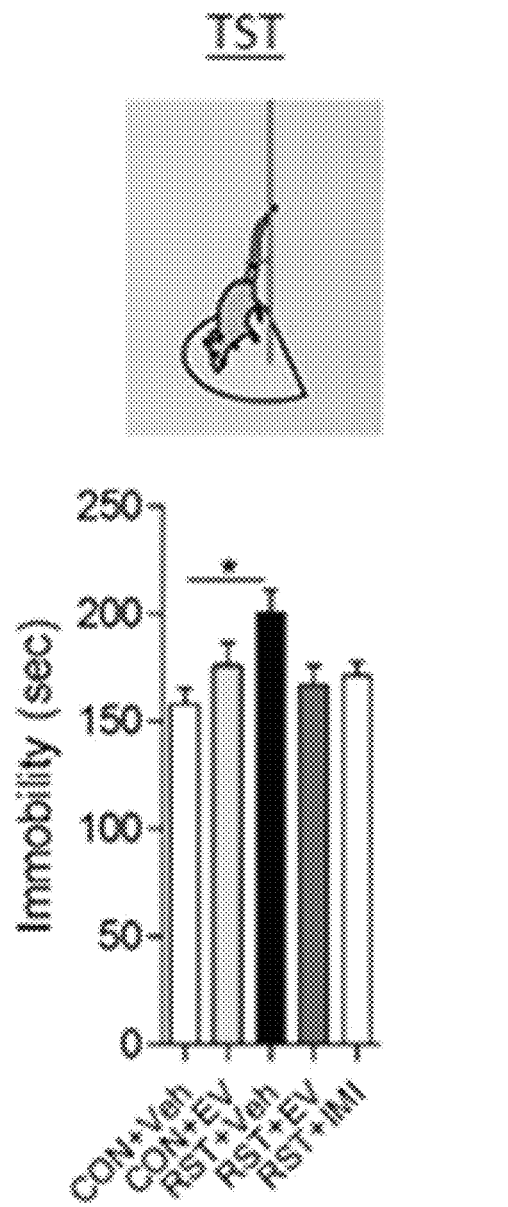
[Fig. 8A]
EV: Lactobacillus plantarum EV
IMI: imipramine

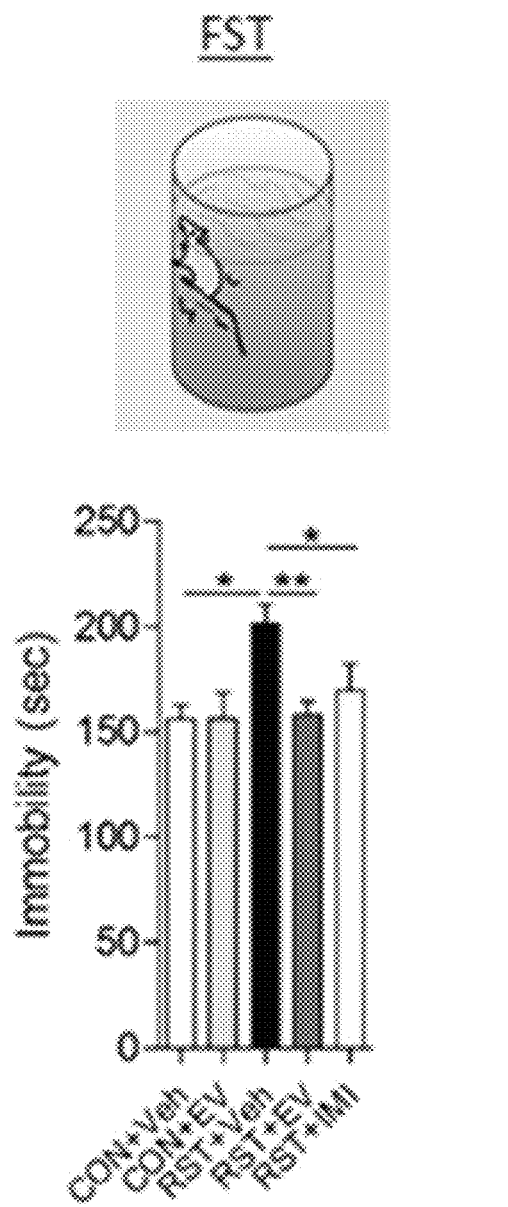
[Fig. 8B]
EV: Lactobacillus plantarum EV
IMI: imipramine

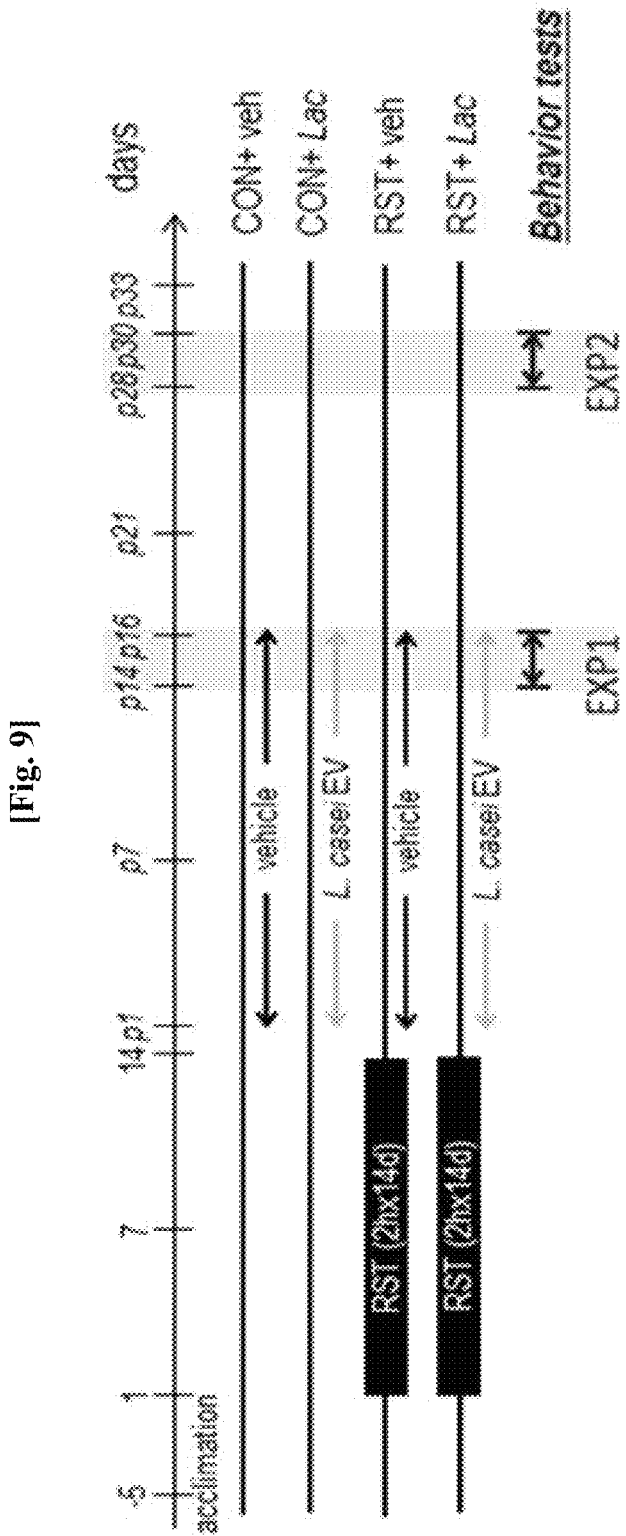
[Fig. 9]

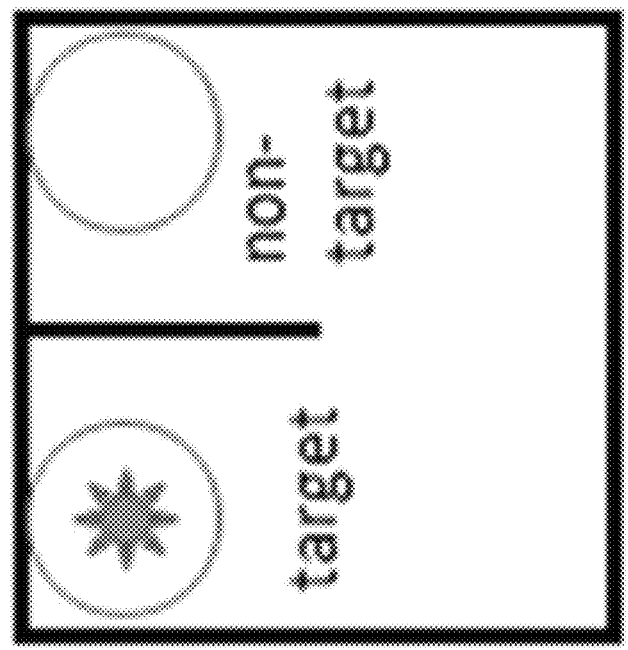
[Fig. 10A]

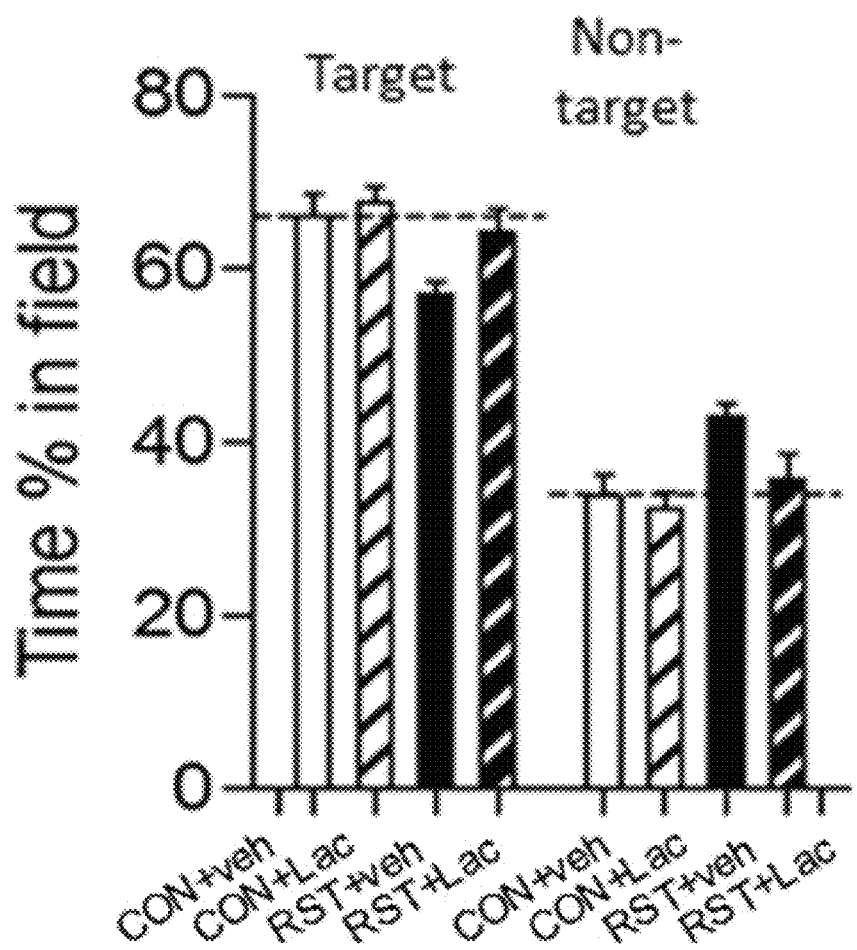
[Fig. 10B]
Lac: Lactobacillus casei EV

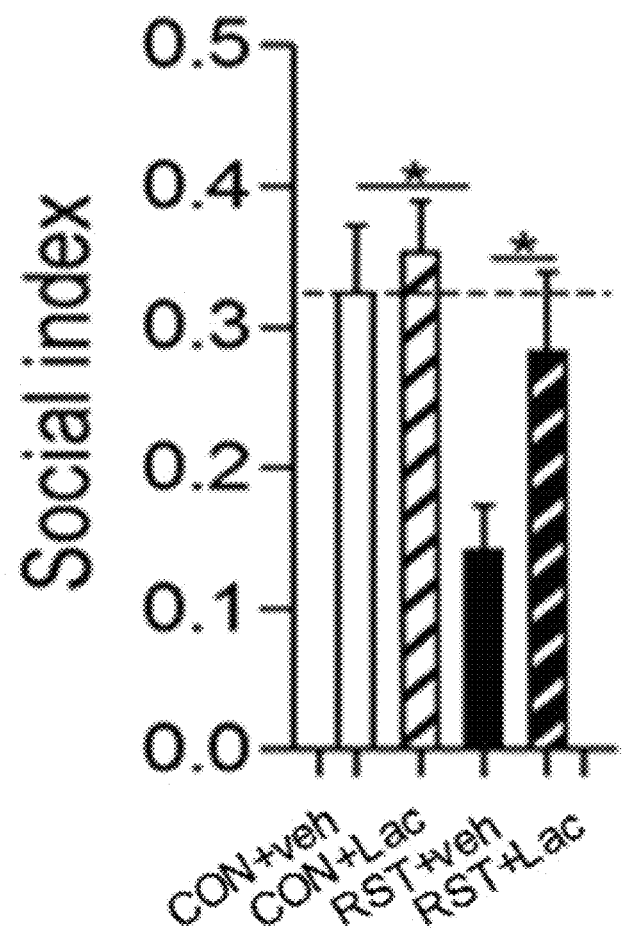
[Fig. 10C]
Lac: Lactobacillus casei EV

[Fig. 11A]
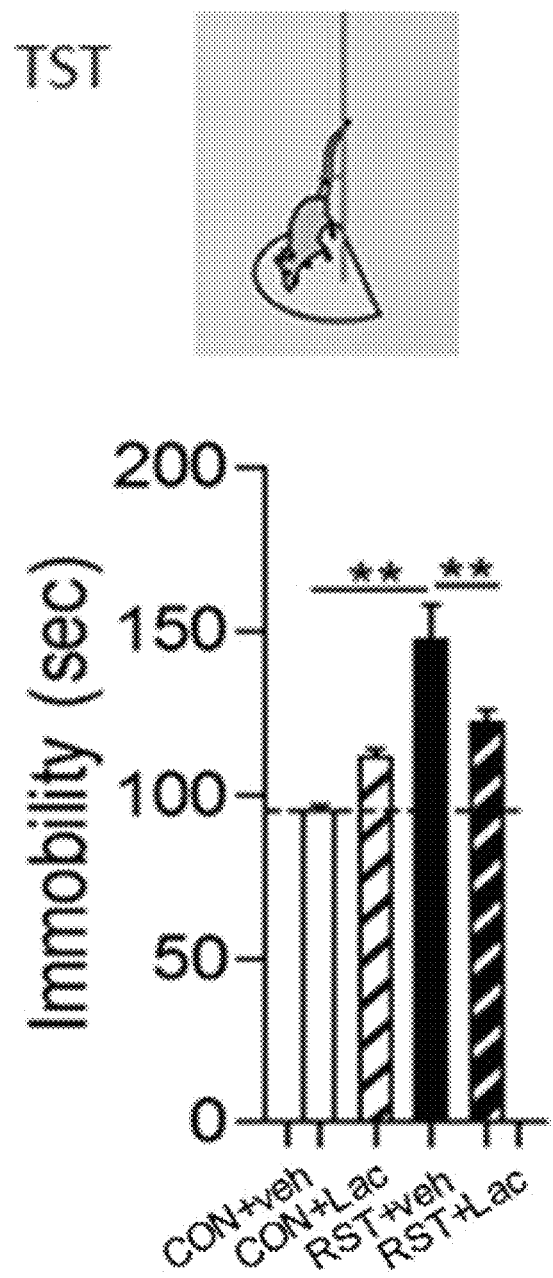
Lac: Lactobacillus casei EV

[Fig. 11B]
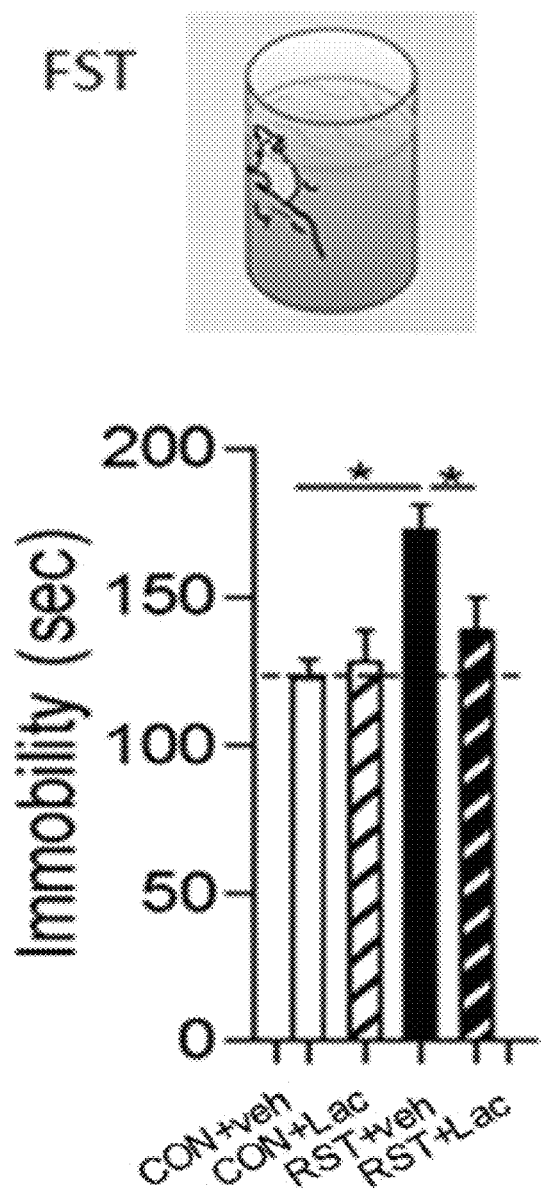
Lac: Lactobacillus casei EV

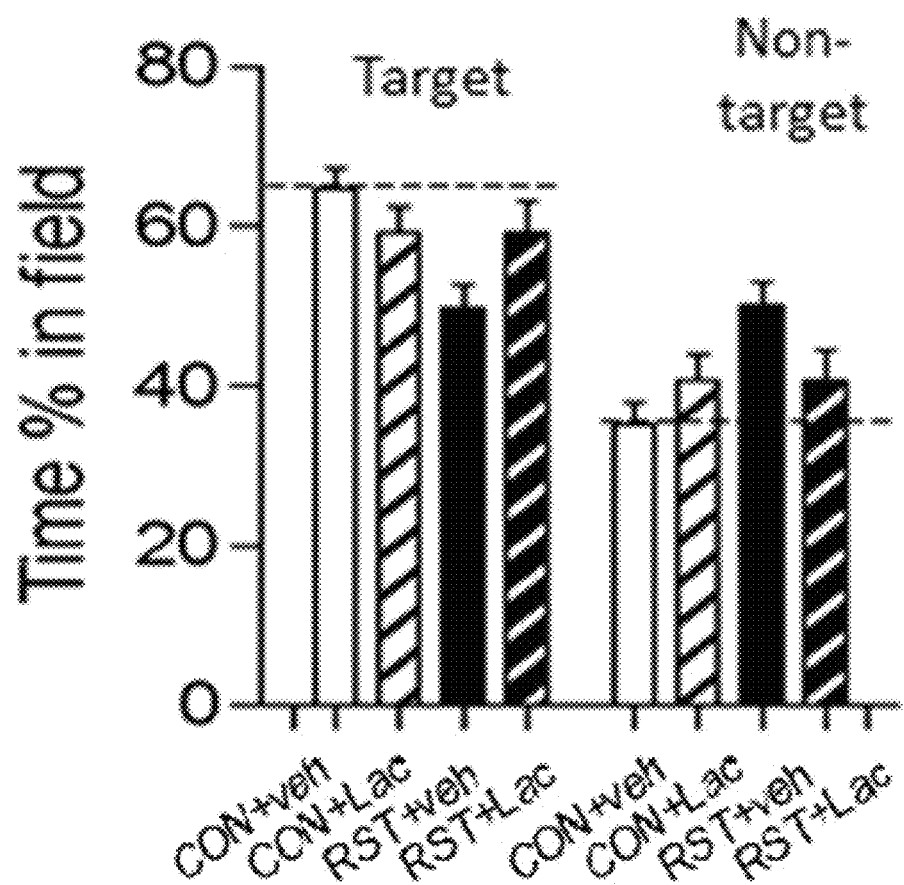
[Fig. 12A]

[Fig. 12B]
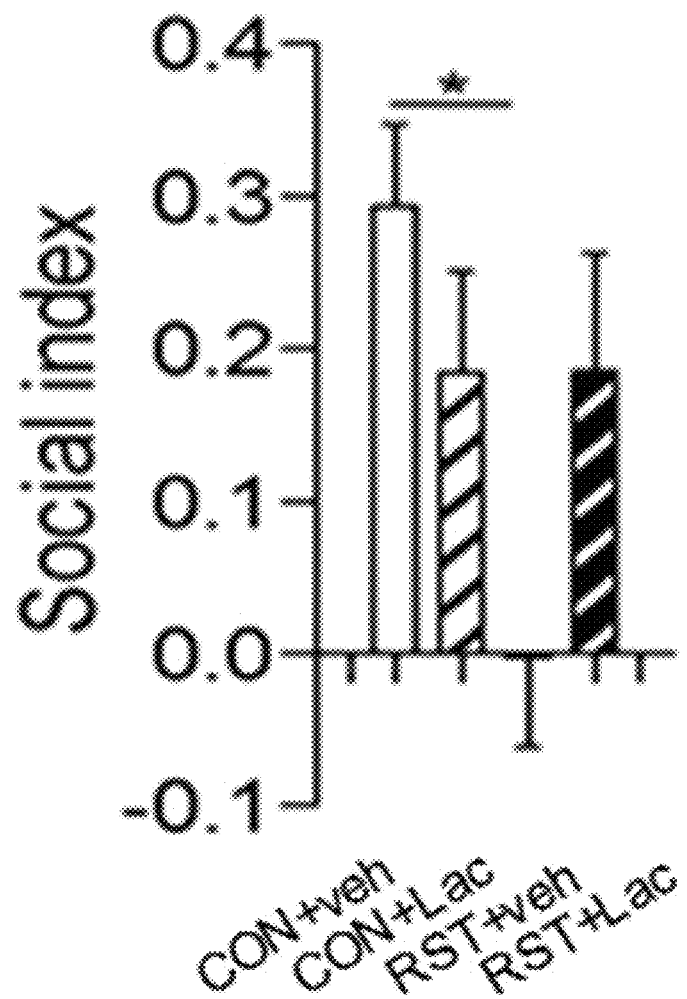

[Fig. 13]
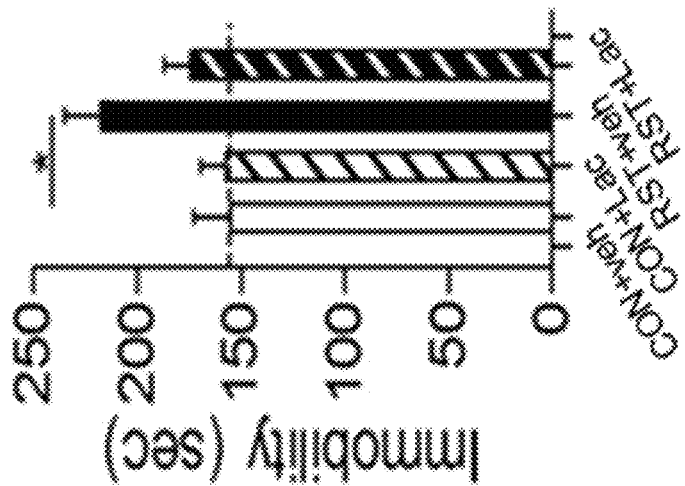
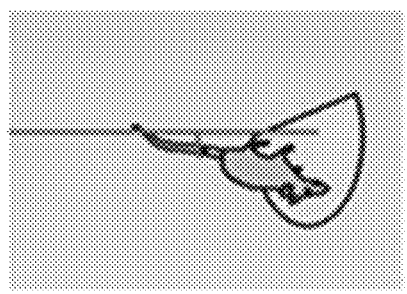

COMPOSITION FOR PREVENTING OR TREATING MENTAL DISORDER, CONTAINING *LACTOBACILLUS* SP. BACTERIA-DERIVED VESICLE

CROSS-REFERENCE TO RELATED APPLICATIONS

This application is the U.S. national phase application filed under 35 U.S.C. § 371 claiming benefit to International Patent Application No. PCT/KR2017/008652, filed on Aug. 9, 2017, which is entitled to priority under to Korean Patent Application No. 10-2016-0103680, filed Aug. 16, 2016, Korean Patent Application No. 10-2017-0085020, filed Jul. 4, 2017 and Korean Patent Application No. 10-2017-0100459, filed Aug. 8, 2017, the disclosure of which is incorporated herein by reference in its entirety.

TECHNICAL FIELD

The present invention relates to a composition for preventing, improving or treating a mental disorder, which includes *Lactobacillus* sp. bacteria-derived vesicles as an active ingredient.

BACKGROUND ART

Depression is a disorder in which negative emotions arise due to the change in brain function for controlling emotions, and over 300 million persons are suffering from depression all over the world. In addition, according to the analysis data of depression for five years from 2005 to 2009 according to the Korea Health Insurance Review and Assessment Service, patients diagnosed with depression and total medical expenses respectively increased 4% and 10.4% annually on average, and the patients diagnosed with depression increased from 435,000 in 2005 to 500,300 in 2009, demonstrating that the number of patients is increasing by approximately 18,000 annually on average. Particularly, the increment in the elderly aged seventy or higher is the highest.

Although various studies have been attempted to establish the cause of depression, the precise neurological pathogenesis has not been defined yet, but it is assumed that there are various causes of depression. Depression involves a chemical imbalance of neurotransmitters such as dopamine, serotonin, norepinephrine, etc. Among the neurotransmitters, serotonin is a neurometabolite found in the cerebrospinal fluid, circulating the brain and serving as a neurotransmitter. Serotonin is closely related to emotional expression, and if it is deficient, due to emotional instability, anxiety increases, and impulsiveness occurs. Therefore, among the drugs currently used as antidepressants, there are several drugs which inhibit reuptake of serotonin so that it is retained in the brain for a long time.

Among the causes of depression, biological, psychological, sociological, pharmacological and pathological factors affect the imbalance of neurotransmitters, and particularly, it has been known that psychological trauma caused by accidents, assault or abuse in childhood is highly likely to develop into depression afterwards. This is caused by protein damage in the human brain under stress. Stressful environments, that is, environmental factors such as the spread of egoism, rapid industrialization, fierce competition and the lack of a social safety net for people falling behind in the competition have been known as causes of depression.

Representative antidepressants used in depression treatment are a tricyclic antidepressant such as imipramine and a selective serotonin reuptake inhibitor (SSRI). However, SSRI-based drugs such as trazodone and mirtazapine have a problem in stability, and particularly, when the elderly take these drugs, a possibility of increased risk of stroke, fractures and death is raised.

Recently, it has been revealed that mental disorders including depression, autism, schizophrenia, etc. are deeply associated with colic. It has been revealed that colic is accompanied by diarrhea and constipation, results in irritable bowel syndrome if repeated, and is associated with gut microbial dysbiosis. When gut microbial dysbiosis occurs due to bad food or the use of antibiotics, intestinal leakage occurs due to cracks in a strong barrier of the large intestine, caused by harmful intestinal microorganisms, and it has been reported that toxins derived from harmful bacteria are systemically absorbed, and thereby depression occurs or worsens [Pharmacotherapy. 2015 October; 35(10):910-6].

*Lactobacillus* sp. bacteria are gram-positive bacilli, which grow well in an aerobic environment as well as an anaerobic environment, and are abundant in fermented food such as kimchi. Although kimchi is over-fermented, while other types of lactic acid bacteria are killed, the *Lactobacillus* sp. bacteria are highly viable bacteria and easily degrade a polysaccharide such as galactose or arabinose.

Bacteria release extracellular vesicles (EVs), often called nanoscale vesicles or nanovesicles, are bilayer membrane structures consisting of proteins and lipids and creating an extracellular environment for the exchange of information between intracellular proteins, lipids, genes, etc. Vesicles derived from gram-positive bacteria such as *Lactobacillus plantarum* or *Lactobacillus casei* also contain bacterial cell wall components such as peptidoglycan and lipoteichoic acid, in addition to bacteria-derived proteins and nucleic acids.

While it has been known that *Lactobacillus plantarum* secretes a factor that inhibits depression in the brain, there was no case of vesicles secreted from *Lactobacillus plantarum* or *Lactobacillus casei* being used for prevention or treatment of a mental disorder such as stress, anxiety disorders, post-traumatic stress disorder (PTSD), panic disorder, depression, autism spectrum disorders, attention deficit hyperactivity disorder (ADHD) or schizophrenia.

DISCLOSURE

Technical Problem

As a result of intensive research to establish the correlation between *Lactobacillus* sp. bacteria-derived vesicles and mental diseases, the inventions confirmed that administration of *Lactobacillus plantarum* and *Lactobacillus casei*-derived vesicles to stress and depression animal models leads to almost equivalent levels of antistress and antidepressant effects as those of the antidepressant imipramine. Based on this, the present invention was completed.

The present invention is directed to providing a composition for preventing, improving or treating a mental disorder, which includes *Lactobacillus* sp. bacteria-derived vesicles as an active ingredient.

However, technical problems to be solved in the present invention are not limited to the above-described problems, and other problems which are not described herein will be fully understood by those of ordinary skill in the art from the following descriptions.

Technical Solution

One aspect of the present invention provides a composition for preventing, improving or treating a mental disorder, which includes *Lactobacillus* sp. bacteria-derived vesicles as an active ingredient.

Another aspect of the present invention provides a health functional food composition for improving a mental disorder, which includes *Lactobacillus* sp. bacteria-derived vesicles as an active ingredient.

Still another aspect of the present invention provides an inhalant composition for preventing or treating a mental disorder, which includes *Lactobacillus* sp. bacteria-derived vesicles as an active ingredient.

According to an exemplary embodiment of the present invention, the mental disorder may be one or more diseases selected from the group consisting of stress, anxiety disorders, PTSD, panic disorder, depression, autism spectrum disorders, ADHD, and schizophrenia.

According to another exemplary embodiment of the present invention, the vesicles may have an average diameter of 10 to 1,000 nm.

According to still another exemplary embodiment of the present invention, the vesicle may be isolated from a culture solution of *Lactobacillus* sp. bacteria.

According to yet another exemplary embodiment of the present invention, the vesicle may be naturally or artificially secreted from *Lactobacillus* sp. bacteria.

According to yet another exemplary embodiment of the present invention, the vesicle may be a vesicle isolated from food produced by adding *Lactobacillus* sp. bacteria.

According to yet another exemplary embodiment of the present invention, the vesicle may be derived from *Lactobacillus plantarum* or *Lactobacillus casei*.

According to yet another exemplary embodiment of the present invention, the vesicle may be derived from *Lactobacillus* sp. bacteria, other than *Lactobacillus plantarum* and *Lactobacillus casei*.

Yet another aspect of the present invention provides a method for preventing or treating a mental disorder, which includes administering the composition to a subject.

Yet another aspect of the present invention provides a use of a *Lactobacillus* sp. bacteria-derived vesicle for preventing or treating a mental disorder.

Advantageous Effects

The inventors confirmed that, when *Lactobacillus plantarum* and *Lactobacillus casei*-derived vesicles were administered to stress and depression animal models, resistance to stress is effectively increased, and treatment of long-term, chronic depressive behavior is effective, and therefore, the *Lactobacillus* sp. bacteria-derived vesicles according to the present invention can be effectively used in developing a medicine or health functional food for preventing, a mental disease such as stress, anxiety disorders, PTSD, panic disorder, depression, autism spectrum disorders, ADHD or schizophrenia, improving a symptom thereof, or treating the disease.

DESCRIPTION OF DRAWINGS

FIG. 1 is a diagram illustrating an experimental protocol for evaluating an antistress effect of *Lactobacillus plantarum*-derived vesicles (EVs) in stress-exposed mouse models [CON or CON+Veh: saline-administered normal mouse group (control, saline-administered control), CON+EV: vesicle-administered normal mouse group, RST+Veh: stress-exposed and saline-administered group, RST+EV: stress-exposed and vesicle-administered group].

FIG. 2A is a diagram illustrating a U-Box test method for measuring sociability for each mouse group to evaluate an antistress effect of *Lactobacillus plantarum*-derived vesicles.

FIG. 2B shows a result of a U-Box test for each mouse group to evaluate an antistress effect of *Lactobacillus plantarum*-derived vesicles.

FIGS. 3A and 3B show results of a tail suspension test (TST) (FIG. 3A) and a forced swim test (FIG. 3B) for each mouse group to evaluate an antistress effect of *Lactobacillus plantarum*-derived vesicles.

FIG. 4 is a diagram illustrating an experimental protocol for evaluating an antistress effect of *Lactobacillus plantarum*-derived vesicles (EVs) in depression-induced mouse models due to chronic stress [CON+Veh: saline-administered normal mouse group, CON+EV: vesicle-administered normal mouse group, RST+Veh: chronic stress-exposed and saline-administered group, RST+EV: chronic stress-exposed and vesicle-administered group, RST+IMI: chronic stress-exposed and imipramine-administered group].

FIG. 5 is a diagram illustrating a U-Box test method for each mouse group as a primary behavioral test for evaluating an antidepressant effect of *Lactobacillus plantarum*-derived vesicles.

FIGS. 6A and 6B show results of a tail suspension test (TST) (FIG. 6A) and a forced swim test (FIG. 6B) for each mouse group as primary behavioral tests for evaluating an antidepressant effect of *Lactobacillus plantarum*-derived vesicles.

FIG. 7 is a diagram illustrating a U-Box test method for each mouse group as a secondary behavioral test for evaluating an antidepressant effect of *Lactobacillus plantarum*-derived vesicles.

FIGS. 8A and 8B show results of a tail suspension test (TST) (FIG. 8A) and a forced swim test (FIG. 8B) for each mouse group as secondary behavioral tests for evaluating an antidepressant effect of *Lactobacillus plantarum*-derived vesicles.

FIG. 9 is a diagram illustrating an experimental protocol for evaluating an antistress and antidepressant effects of *Lactobacillus casei*-derived vesicles (*L. casei* EVs) in stress-exposed mouse models [CON+Veh: saline-administered control, CON+Lac: vesicle-administered normal mouse group, RST+Veh: stress-exposed and saline-administered group, RST+Lac: stress-exposed and vesicle-administered group].

FIGS. 10A, 10B and 10C show results of evaluating a target-searching behavior (FIG. 10B) and a social index (FIG. 10C) by performing a U-Box test (FIG. 10A) for each mouse group as primary behavioral tests for evaluating an antistress effect of *Lactobacillus casei*-derived vesicles.

FIGS. 11A and 11B show results of a tail suspension test (TST) (FIG. 11A) and a forced swim test (FIG. 11B) for each mouse group as primary behavioral tests for evaluating an antistress effect of *Lactobacillus casei*-derived vesicles.

FIGS. 12A and 12B show results of evaluating a target-searching behavior (FIG. 12A) and a social index (FIG. 12B) by performing a U-Box test for each mouse group as secondary behavioral tests for evaluating an antistress preventing effect of *Lactobacillus casei*-derived vesicles.

FIG. 13 shows a result of a tail suspension test (TST) for each mouse group as a secondary behavioral test for evaluating an antidepressant effect of *Lactobacillus casei*-derived vesicles.

MODES OF THE INVENTION

As a result of intensive research to examine the correlation between *Lactobacillus* sp. bacteria-derived vesicles-derived vesicles and a mental disorder, the inventors found that the administration of *Lactobacillus* sp. bacteria-derived vesicles in stress and depression animal models induced almost equivalent levels of antistress and antidepressant effects as those of the antidepressant imipramine. Based on this, the present invention was completed.

In an exemplary embodiment of the present invention, compared with an only stress-exposed mouse, an antistress effect in the nanovesicle-administered mouse was confirmed (see Example 1) by performing three types of behavior tests, that is, a U-BOX test for measuring sociability, a tail suspension test and a forced swim test after *Lactobacillus plantarum*-derived vesicles are administered to restraint stress-exposed mouse models (see Example 1).

In another exemplary embodiment of the present invention, *Lactobacillus plantarum*-derived vesicles are administered to a mouse model in which depressive behavior is induced by chronic stress, and then the above-mentioned three types of behavior tests are performed, thereby confirming that the vesicles exhibit an antidepressant effect (see Example 2).

In still another exemplary embodiment of the present invention, *Lactobacillus casei*-derived vesicles are administered to a mouse model exposed to restraint stress, and then the above-mentioned three types of behavior tests are performed two weeks and four weeks after stress induction, thereby confirming that the vesicles exhibit antistress and antidepressant effects (see Example 3).

The present invention provides a pharmaceutical composition for preventing or treating a mental disorder, which includes *Lactobacillus* sp. bacteria-derived vesicles-derived vesicles as an active ingredient.

The term "mental disorder" used herein refers to a pathological mental state that affects a person's thoughts, feelings and behaviors, and encompasses a condition of mental function impairment. In the present invention, the mental disorder includes stress, anxiety disorders, PTSD, panic disorder, depression, autism spectrum disorders, ADHD, and schizophrenia.

The term "stress" used herein is a non-specific biological response occurring in the body with respect to various injuries and stimuli to a living body, and was first named by the Canadian endocrinologist H. Selye. The stress response is a response of protecting the body from a stimulation hormone, adrenaline, or other hormones secreted into the blood, and provides power and energy to cope with danger or avoid the situation. General symptoms caused by stress vary, and are classified into four categories including physical symptoms such as fatigue, headaches, insomnia, stomach pain, abdominal pain and vomiting, mental symptoms such as concentration or memory loss, indecisiveness and emptiness, emotional symptoms such as anxiety, hypersensitivity, depression, anger and frustration, and behavioral symptoms such as restlessness, nervous habits and smoking.

The term "depression (depressive disorder)" used herein refers to a disease having depression and desensitization as main symptoms, causing various cognitive and psychosomatic symptoms, resulting in deterioration of daily functions. Depression is known to be caused by a biochemical factor such as an imbalance of a neurotransmitter or a hormone, a genetic factor, and an environmental factor such as high stress. Depression has been known to be prevented by aid such as stress regulation, friendship in time of crisis, social support, etc.

The term "prevention" used herein refers to all actions of inhibiting a mental disorder or delaying the onset thereof by administration of the pharmaceutical composition according to the present invention.

The term "treatment" used herein refers to all actions involved in alleviating or beneficially changing the symptoms of a mental disorder by administration of the pharmaceutical composition according to the present invention.

The vesicles of the present invention may be isolated from a culture solution of *Lactobacillus* sp. bacteria or food produced by adding *Lactobacillus* sp. bacteria, and naturally or artificially released from *Lactobacillus* sp. bacteria, but the present invention is not limited thereto.

A method of isolating vesicles from a culture solution or fermented food of *Lactobacillus* sp. bacteria according to the present invention is not particularly limited as long as it includes vesicles. For example, vesicles may be isolated by centrifugation, high speed centrifugation, filtration, gel filtration chromatography, free-flow electrophoresis, capillary electrophoresis, or a combination thereof. The method may additionally include washing for removing impurities and concentration of the obtained vesicles.

The vesicles isolated by the method in the present invention may have an average diameter of 10 to 1,000 nm, but the present invention is not limited thereto.

The pharmaceutical composition according to the present invention may include *Lactobacillus* sp. bacteria-derived vesicles-derived vesicles as an active ingredient, and also include a pharmaceutically acceptable carrier. The pharmaceutically acceptable carrier is generally used in formulation, and includes saline, distilled water, Ringer's solution, buffered saline, cyclodextrin, a dextrose solution, a maltodextrin solution, glycerol, ethanol, liposomes, etc., but the present invention is not limited thereto. If needed, the pharmaceutically composition may further include other conventional additives including an antioxidant, a buffer, etc. In addition, by additionally adding a diluent, a dispersant, a surfactant, a binder or a lubricant, the pharmaceutical composition may be formulated as an injectable form such as an aqueous solution, an emulsion or a suspension, a pill, a capsule, a granule or a tablet. Suitable pharmaceutically acceptable carriers and their formulations may be formulated according to each ingredient using a method disclosed in the Remington's Pharmaceutical Science. The pharmaceutical composition of the present invention is not limited in dosage form, and thus may be formulated as an injection, an inhalant, a dermal preparation for external use, or an oral preparation.

The pharmaceutical composition of the present invention may be administered orally or non-orally (e.g., intravenously, subcutaneously, percutaneously, nasally or intratracheally) according to a desired method, and a dose of the pharmaceutical composition of the present invention may be selected according to a patient's condition and body weight, severity of a disease, a dosage form, an administration route and duration by those of ordinary skill in the art.

The composition according to the present invention is administered at a pharmaceutically acceptable amount. In the present invention, the "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

Specifically, the effective amount of the composition according to the present invention may be changed according to a patient's age, sex or body weight, and generally, 0.001 to 150 mg, and preferably 0.01 to 100 mg per kg of body weight may be administered daily or every other day, or one to three times a day. However, the effective amount may be increased or decreased depending on the route of administration, the severity of obesity, sex, a body weight or age, and thus it does not limit the scope of the present invention in any way.

In addition, the present invention provides a health functional food composition for improving a mental disorder, which includes *Lactobacillus* sp. bacteria-derived vesicles as an active ingredient.

The term "alleviation" used herein refers to all types of actions that at least reduce parameters related to a condition to be treated, for example, a degree of a symptom.

In the health functional food composition of the present invention, the active ingredient may be directly added to food or used together with other food or food ingredients, and may be suitably used according to a conventional method. The mixing amount of the active ingredient may be suitably determined according to the purpose (for alleviation) of use thereof. Generally, in the production of food or beverages, the composition of the present invention is added at 15 wt % or less, and preferably 10 wt % or less with respect to the raw materials. However, in long-term consumption for health and hygiene or health control, the amount of the composition may be the same as or lower than the above-mentioned range.

The health functional food composition of the present invention has no limitation to components, other than containing the active ingredient as an essential component at an indicated proportion, and may contain various flavoring agents or natural carbohydrates like a conventional beverage. Examples of the above-mentioned natural carbohydrates include conventional sugars, for example, monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. As the sweeteners, natural sweeteners [thaumatin, *stevia* extract (e.g., rebaudioside A, glycyrrhizin, etc.)] and synthetic sweeteners (saccharin, aspartame, etc.) may be advantageously used. The proportion of the natural carbohydrate may be suitably determined by the choice of those of ordinary skill in the art.

The health functional food composition of the present invention may contain various nutrients, vitamins, minerals (electrolytes), flavoring agents including synthetic and natural flavoring agents, coloring agents, fillers (cheese, chocolate, etc.), pectic acid and a salt thereof, alginic acid and a salt thereof, organic acids, protective colloidal thickening agents, pH adjusters, stabilizers, preservatives, glycerin, alcohols, or carbonizing agents used in carbonated beverages, and such components may be used independently or in combination. A proportion of such an additive may also be suitably selected by those of ordinary skill in the art.

The present invention also provides an inhalant composition for preventing or treating a mental disorder, which includes *Lactobacillus* sp. bacteria-derived vesicles as an active ingredient.

In the inhalant composition of the present invention, the active ingredient may be directly added to an inhalant or used together with other ingredients, and may be suitably used according to a conventional method. A mixing amount of the active ingredient may be suitably determined according to the purpose of use thereof (for prevention or treatment).

The present invention provides a method for preventing or treating a mental disorder, which includes administering a composition including *Lactobacillus* sp. bacteria-derived vesicles as an active ingredient to a subject.

The term "subject" used herein refers to a subject in need of treatment, and more specifically, a mammal such as a human, or a non-human primate, a mouse, a rat, a dog, a cat, a horse and a cow.

Hereinafter, to help in understanding the present invention, exemplary examples will be suggested. However, the following examples are merely provided to more easily understand the present invention, and not to limit the present invention.

EXAMPLES

Example 1. Confirmation of Antistress Effect by *Lactobacillus* sp. Bacteria-Derived Vesicles Through an experiment using a mouse, when *Lactobacillus plantarum*-derived nanovesicles are administered, it was examined whether the occurrence of depressive behavior due to stress is interrupted. To this end, according to the experimental procedure shown in FIG. 1, 7-week-old male C57BL/6 mice were purchased and randomly divided into four groups, that is, a normal mouse group to which saline (0.9% Saline, 100 μl) was administered for 14 days (CON or CON+Veh), a normal mouse group to which nanovesicles (2 μg/mouse/100 μl) are administered (CON+EV), a group in which saline (0.9% Saline, 100 μl) was administered to a restraint stress (RST)-exposed mouse for 2 hours a day for 14 days (RST+Veh), and a group in which nanovesicles (EV, 2 ug/mouse/100 μl) are administered to a restraint stress-exposed mouse for two hours a day for 14 days (RST+EV) to perform the experiment. Afterward, a U-BOX test for measuring sociability, a tail suspension test (TST) and a forced swim test (FST) were sequentially performed to evaluate an antistress effect according to the administration of nanovesicles.

First, a U-BOX test was performed on four groups of mice which had undergone the above-described experiment. As illustrated in the diagram of FIG. 2A, the test was an experimental method for confirming how long a target mouse made contact with one side of a U-shaped field in which the target mouse was placed inside a wire mesh, and the other side in which a wire mesh was placed without a target mouse. As a result of the experiment, as shown in FIG. 2B, during habituation (non-target condition, 5 min), the mouse exhibited a similar probability of staying on both sides, but in an actual behavior test, which is a target condition, performed for 10 minutes, a different result was shown per group. In other words, it was confirmed that, in the control (CON+Veh) and the group in which nanovesicles were administered to the control (CON+EV), the time spent in the target space (Target) was increased, compared with the time spent in a non-target space (Non-target), and in the restraint stress-exposed group (RST+Veh), a mouse spent less time in the target space. On the other hand, it was confirmed that, in the stress-exposed and nanovesicle (EV)-administered group (RST+EV), the time spent in the target space was increased to a level similar to that of the control.

Subsequently, as a result of performing each of the tail suspension test (FIG. 3A) and the forced swim test (FIG. 3B), it was confirmed that, compared with the control (CON+Veh), immobility was increased in the restraint stress-exposed group (RST+Veh), whereas in the stress-exposed and nanovesicle-administered group (RST+EV), immobility was decreased.

The above-mentioned results showed that, when *Lactobacillus plantarum*-derived vesicles were administered to the stress-exposed mouse model, an excellent antistress effect was exhibited.

Example 2. Confirmation of Antistress Effect by *Lactobacillus plantarum*-Derived Vesicles In addition to the result of Example 1, it was evaluated whether depressive behavior induced by chronic stress can be restored by the administration of *Lactobacillus plantarum*-derived nanovesicles. To this end, as shown in the diagram of FIG. 4, 7-week-old male C57BL/6 mice were purchased and randomly divided into five groups, that is, a normal mouse group to which saline (0.9% Saline, 100 μl) was administered for 14 days (CON or CON+Veh), a normal mouse group to which nanovesicles (EV, 2, 4 or 6 μg/mouse/100 μl) were administered (CON+EV), a group in which saline (0.9% Saline, 100 μl) was administered to a chronic stress-exposed mouse for 14 days (RST+Veh), a group in which nanovesicles (EV, 2, 4 or 6 μg/mouse/100 μl) were administered to a chronic stress-exposed mouse for 14 days (RST+EV), and a group in which imipramine (IMI, 20 mg/kg/day) was administered to a chronic stress-exposed mouse for 14 days (RST+IMI) to perform the experiment, and then three types of depressive behavior tests were sequentially performed as described in Example 1. In addition, two weeks after the primary behavioral test (Behavior test-1), a secondary behavioral test (Behavior test-2) was performed in the same order as described above. In addition, when nanovesicles were input, the nanovesicles were administered daily after the end of stress induction, and the nanovesicles were administered at gradually increasing amounts, for example, at 2 μg/mouse/100 μl from day 1 (p1) to day 4 (p4), 4 μg/mouse/100 μl from day 5 (p5) to day 6 (p6), and 6 μg/mouse/100 μl from day 7 (p7) to day 14 (p14).

First, as a result of the U-BOX test, as shown in FIG. 5, during habituation, there was no difference in time spent in both spaces between the mouse groups, but under the target condition, compared with the control (CON+Veh), the stress-exposed control (RST+Veh) was decreased in time spent in the target space (Target). On the other hand, in the stress-exposed and nanovesicle-administered group (RST+EV) and the stress-exposed and imipramine-administered group (RST+IMI), it was confirmed that time spent in the target space was restored to a control level.

Subsequently, as shown in FIG. 6, as the results of the tail suspension test (FIG. 6A) and the forced swim test (FIG. 6B, it was confirmed that, compared with the control (CON+Veh), the stress-exposed group (RST+Veh) was significantly increased in immobility, but in the stress-exposed and nanovesicle-administered group (RST+EV) and the stress-exposed and imipramine-administered group (RST+IMI), the immobility time was decreased to a control level.

Further, as the result of performing the same behavior tests again two weeks after the primary behavioral test shown in FIGS. 5 and 6, as shown in FIG. 7, like the primary U-BOX test result, a secondary test result also showed that, in the stress-exposed and nanovesicle-administered group (RST+EV) and the stress-exposed and imipramine-administered group (RST+IMI), the time spent in the target space was restored to a level similar to that of the control. In addition, as shown in FIG. 8, the secondary tail suspension test (FIG. 8A) and the forced swim test (FIG. 8B) showed that, like the primary test result, in the stress-exposed and nanovesicle-administered group (RST+EV) and the stress-exposed and imipramine-administered group (RST+IMI), immobility time was decreased to the control level.

From the above-described results, it can be seen that the administration of nanovesicles to the mouse model in which depression was induced by chronic stress exhibits an antidepressant therapeutic effect.

Example 3. Confirmation of Antistress and Antidepressant Effects by *Lactobacillus casei*-Derived Nanovesicles Through an experiment using a mouse, when *Lactobacillus casei*-derived nanovesicles were administered, it was examined whether the occurrence of depressive behavior due to stress is interrupted. To this end, according to the experimental procedure shown in FIG. 9, 8-week-old male C57BL/6 mice were purchased and randomly divided into four groups, that is, a normal mouse group to which saline (0.9% Saline, 100 μl) was administered for 14 days (CON+Veh), a normal mouse group to which nanovesicles (11 ug/mouse/100 μl) were administered (CON+Lac), a group in which saline (0.9% Saline, 100 μl) was administered to a restraint stress (RST)-exposed mouse for 2 hours a day for 14 days (RST+Veh), and a group in which nanovesicles (EV, 11 μg/mouse/100 μl) were administered to a restraint stress-exposed mouse for 2 hours daily for 14 days (RST+Lac), to perform the experiment. Afterward, a U-BOX test for measuring sociability, a tail suspension test (TST) and a forced swim test (FST) were sequentially performed two weeks after stress exposure and four weeks after stress exposure to evaluate antistress and antidepressant effects according to the administration of nanovesicles.

First, for the four groups of mice that had undergone the above-described experiment, a U-BOX test (sociability test) was performed two weeks after the stress exposure. As shown in the diagram of FIG. 10A, the test was an experimental method for confirming how long a target mouse made contact with one side of a U-shaped field in which the target mouse was placed inside a wire, and the other side in which a wire mesh was placed without a target mouse.

As a result of the experiment, as shown in FIG. 10B, in the control (CON+Veh) and the group in which nanovesicles were administered to the control (CON+Lac), the time spent in the target space (Target) was increased, compared with the time spent in a non-target space (Non-target), but in the restraint stress-exposed group (RST+Veh), the time spent in a target space was shorter compared to that of the control. On the other hand, it was confirmed that, in the stress-exposed and nanovesicle-administered group (RST+Lac), the time spent in the target space was increased to a level similar to that of the control.

In addition, as shown in FIG. 10C, compared with the control, the social index calculated by the U-BOX test was significantly decreased in the restraint stress-exposed group (RST+Veh), and restored to a level similar to that of the control in the restraint stress-exposed and nanovesicle-administered group (RST+veh).

Subsequently, as a result of performing each of the tail suspension test (FIG. 11A) and the forced swim test (FIG. 11B), it was confirmed that, compared with the control (CON+Veh), immobility was increased in a restraint stress-exposed group (RST+Lac), whereas in the restraint stress-exposed and nanovesicle-administered group (RST+Lac), immobility was significantly decreased. It can be seen that, when *Lactobacillus casei*-derived vesicles were administered to a stress-exposed mouse model, an excellent antistress effect was exhibited.

Further, for the four groups of mice that had undergone the above-described experiment, a U-BOX test (sociability test) was performed 4 weeks after the stress exposure. As shown in FIG. 12A, the time spent in the target space (Target) was longer than the time spent in the non-target space (Non-target) in the control (CON+Veh) and the group in which nanovesicles were administered to the control (CON+Lac), but the time spent in the target space in the restraint stress-exposed group (RST+Veh) was shorter compared to that of the control. On the other hand, it was confirmed that, in the restraint stress-exposed and nanovesicle-administered group (RST+Lac), the time spent in the target space was increased to a level similar to that of the control.

In addition, as shown in FIG. 12B, compared with the control, the social index was significantly decreased in the restraint stress-exposed group (RST+Veh) and restored to a level similar to that of the control in the restraint stress-exposed and nanovesicle-administered group (RST+veh).

Moreover, as shown in FIG. 13, as a result of the tail suspension test, it was confirmed that, compared with the control (CON+Veh), immobility was increased in the restraint stress-exposed group (RST+Lac), whereas in the restraint stress-exposed and nanovesicle-administered group (RST+Lac), immobility was decreased. This showed that when *Lactobacillus casei*-derived vesicles were administered to a stress-exposed mouse model, an excellent antidepressant effect was exhibited.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

The present invention relates to a composition for preventing, improving or treating a mental disorder, which includes *Lactobacillus* sp. bacteria-derived vesicles-derived vesicles as an active ingredient, and according to the present invention, a composition for preventing, improving or treating a mental disorder, which includes *Lactobacillus* sp. bacteria-derived vesicles as an active ingredient is provided, and thus it is expected that the composition will be effectively used in development of a medicine or health functional food for preventing a mental disorder, improving a symptom thereof, or treating the mental disorder.

The invention claimed is:

1. A method for preventing or treating a mental disorder, comprising:
    administering an inhalant composition consisting of *Lactobacillus* sp. bacteria-derived vesicles as an active ingredient and a pharmaceutically acceptable carrier or inhalant ingredients to a subject in need thereof;
    wherein the vesicles are isolated from a culture solution of *Lactobacillus* sp. bacteria, food produced by adding *Lactobacillus* sp. bacteria, or a combination thereof,
    wherein the vesicles are derived from *Lactobacillus plantarum*, *Lactobacillus casei*, or a combination thereof; and
    wherein the mental disorder is a disease selected from the group consisting of stress, anxiety disorders, post-traumatic stress disorder (PTSD), panic disorder, autism spectrum disorders, attention deficit hyperactivity disorder (ADHD), and schizophrenia.

2. The method of claim 1, wherein the vesicles have an average diameter of 10 to 1,000 nm.

3. The method of claim 1, wherein the vesicles were naturally or artificially released from *Lactobacillus* sp. bacteria.

4. A method for improving a mental disorder, comprising:
    administering an inhalant composition consisting of *Lactobacillus* sp. bacteria-derived vesicles as an active ingredient and a pharmaceutically acceptable carrier or inhalant ingredients to a subject in need thereof;
    wherein the vesicles are isolated from a culture solution of *Lactobacillus* sp. bacteria, food produced by adding *Lactobacillus* sp. bacteria, or a combination thereof,
    wherein the vesicles are derived from *Lactobacillus plantarum*, *Lactobacillus casei*, or any combination thereof; and
    wherein the mental disorder is a disease selected from the group consisting of stress, anxiety disorders, post-traumatic stress disorder (PTSD), panic disorder, autism spectrum disorders, attention deficit hyperactivity disorder (ADHD), and schizophrenia.

5. The method of claim 4, wherein the vesicles have an average diameter of 10 to 1,000 nm.

6. The method of claim 4, wherein the vesicles were naturally or artificially released from *Lactobacillus* sp. bacteria.

* * * * *